US00PP23202P2

(12) United States Plant Patent
Klemm et al.

(10) Patent No.: US PP23,202 P2
(45) Date of Patent: Nov. 20, 2012

(54) **NEW GUINEA *IMPATIENS* PLANT NAMED 'KLENI10117'**

(50) Latin Name: *Impatiens hawkeri*
Varietal Denomination: KLENI10117

(75) Inventors: Nils Klemm, Stuttgart (DE); Katinka Wilde, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 13/136,178

(22) Filed: Jul. 26, 2011

(51) Int. Cl.
*A01H 5/00* (2006.01)

(52) U.S. Cl. ..... Plt./318.2

(58) Field of Classification Search ..... Plt./318.2
See application file for complete search history.

*Primary Examiner* — Annette Para

(74) *Attorney, Agent, or Firm* — Jondle & Associates, P.C.

(57) ABSTRACT

A new variety of New Guinea *Impatiens* plant named 'KLENI10117', particularly distinguished by its suitability for growth in small pots and high density production, very good branching, and nice green foliage, is described.

1 Drawing Sheet

Genus and species: *Impatiens hawkeri.*
Variety denomination: 'KLENI10117'.

BACKGROUND OF THE NEW PLANT

The present invention comprises a new and distinct variety of New Guinea *Impatiens*, botanically known as *Impatiens hawkeri*, and hereinafter referred to by the variety name 'KLENI10117'. The new variety originated from a hybridization made in November 2007 in Kenya. The female parent was the proprietary *Impatiens* plant 'KLENI08109' (unpatented), while the male parent was the proprietary *Impatiens* plant 'TW1' (unpatented). A single plant section was subsequently chosen for further evaluation and asexual propagation.

The new variety was first propagated in the Summer of 2008 in Stuttgart, Germany and has been asexually reproduced repeatedly by vegetative cuttings in Stuttgart, Germany for 6 generations. 'KLENI10117' has been found to retain its distinctive characteristics through these successive asexual propagations.

Plant Breeder's Rights for this variety were applied for in Switzerland on Jun. 29, 2010 and in the European Union, on Jul. 9, 2010. 'KLENI10117' has not been made publicly available more than one year prior to the filing date of this application.

SUMMARY OF THE INVENTION

The following are the most outstanding and distinguishing characteristics of this new variety when grown under normal horticultural practices in a glass greenhouse in Stuttgart, Germany.

1. Good performance in small pots and high density production;
2. Very good branching;
3. Nice green foliage; and
4. Medium-sized white flowers.

DESCRIPTION OF PHOTOGRAPH

This new variety of New Guinea *Impatiens* plant is illustrated by the accompanying photograph which shows the overall plant habit including blooms, buds, and foliage of the plant. The colors shown are as true as can be reasonably obtained by conventional photographic procedures. The photograph is of a plant about 18 weeks old, grown from rooted cuttings in a 10.5 centimeter pot in a glass-covered greenhouse in 2010 in Stuttgart, Germany, under conditions which approximate those generally used in normal commercial practice.

DESCRIPTION OF THE NEW VARIETY

The following detailed descriptions set forth the distinctive characteristics of 'KLENI10117'. The data which defines these characteristics were collected from asexual reproductions carried out in Stuttgart, Germany. The plant history was taken in 2010 on 18 week old plants which were planted as rooted cuttings in 10.5 cm pots, and then grown in a glass-covered greenhouse. Color readings were taken under artificial light in the greenhouse. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Balsaminaceae.
- *Botanical.*—*Impatiens hawkeri.*
- *Common name.*—New Guinea *Impatiens.*

Parentage:
- *Female parent.*—The proprietary New Guinea *Impatiens* plant, 'KLENI08109' (unpatented).
- *Male parent.*—The proprietary New Guinea *Impatiens* plant, 'TW1' (unpatented).

Growth:
- *Growth and branching habit.*—Compact; round.
- *Height.*—13 cm.
- *Width.*—26 cm.
- *Propagation.*—Vegetative cuttings.
- *Time from rooted cutting to finish.*—35-45 days in the Spring.
- *Time to initiate and develop roots.*—21 to 28 days.

Branches:
*Average number.*—20.
*Length of branches.*—10.0 cm.
*Internode length.*—2.0 cm.
*Diameter of branches.*—0.5 cm.
*Stem color.*—RHS 146C.

Leaves:
*Arrangement.*—Base of the plant: Opposite. Middle and upper section of the plant: Whorled.
*Size.*—Length: 7.0 cm. Width: 2.0 cm.
*Shape.*—Oblong to lanceolate.
*Apex.*—Acuminate.
*Base.*—Acuminate.
*Margin.*—Shallowly serrate.
*Color (mature leaves).*—Upper surface: RHS 139A. Lower surface: RHS 139C.
*Color (immature leaves).*—Upper surface: RHS 143A. Lower surface: RHS 143B.
*Texture (both surfaces).*—Leathery, glossy.
*Venation.*—Presence: Present. Color (both surfaces): RHS 144D. Anthocyanin coloration: absent.
*Variegation.*—Absent.
*Petioles.*—Length: 1.2 cm. Diameter: 0.4 cm. Color (both surfaces): RHS 144D. Texture (both surfaces): Smooth.

Peduncle:
*Color.*—RHS 144D.
*Size.*—Length: 4.0 cm. Diameter: 0.2 cm.
*Texture.*—Smooth.

Flower buds:
*Shape.*—Ovoid; completely closed: drop shaped.
*Size.*—Length: 1.2 cm. Diameter: 1.2 cm.
*Color.*—RHS 145B.

Inflorescence:
*Blooming habit.*—Continuous.
*Inflorescence type.*—Single flowers arranged in clusters arising from the leaf axils; flowers positioned above the foliage; flowers face upward and outward.
*Number of flowers per node.*—1 to 4 flowers and 2 buds.
*Flowering season.*—April to Fall.
*Lastingness of individual blooms on the plant.*—14 to 21 days.

Flowers:
*Corolla form.*—Single.
*Number of petals.*—5.
*Shape of corolla.*—Round to oval.
*Corolla size.*—Length.—5.5 cm. Width.—6.0 cm. Depth.—0.5 cm.

Petals:
*Shape.*—Cordate.
*Apex.*—Medium-sized incision at apex.
*Base.*—Round to acute.
*Margin.*—Entire.
*Size.*—Upper petals: Length: 2.2 cm. Width: 3.2 cm. Lateral petals: Length: 2.3 cm. Width: 2.4 cm. Lower petals: Length: 3.2 cm. Width: 2.5 cm. General color description: White.
*Color (both surfaces).*—RHS 155C.
*Color of eye zone.*—RHS 155C.
*Texture (both surfaces).*—Satiny, smooth.

Spur:
*Shape.*—Oblong to acute.
*Color.*—RHS 157B.
*Size.*—Length: 4.5 cm. Diameter at proximal end: 0.3 cm. Diameter at distal end: 0.1 cm.

Sepals:
*Quantity per flower.*—4.
*Lateral sepals.*—Shape: Acuminate; entire. Length: Approximately 1.2 cm. Width: Approximately 0.4 cm.
*Lower sepals.*—Shape: Base of sepal modified to a spur. Length: 1.5 cm. Width: 1.7 cm. Apex: Acuminate.
*Surface texture (both upper and lower surfaces).*—Glabrous.
*Color (both upper and lower surfaces).*—Lateral: RHS 144B. Lower: RHS 157B.

Reproductive organs:
*Stamens.*—Number: 5 stamens are fused and form a cap over the ovary. Anther color: RHS 10D. Stamen color (upper surface color): RHS 155B. Pollen color: RHS 155D. Pollen amount: Medium.
*Pistils.*—Number per flower: 1. Style and stigma: Hair-like. Arrangement: Arranged in a circle on top of ovary. Color: RHS 155A. Ovary: Shape: Ovate. Length: 0.6 cm. Color: RHS 143A.

Fruit and seed set: Seed production has not been observed.

Disease and insect resistance: Plants have medium tolerance to red spider mite.

COMPARISON WITH PARENTAL AND COMMERCIAL VARIETIES

'KLENI10117' differs from the female parent 'KLENI08109' (unpatented) by having very good branching and is very early, while 'KLENI08109' has good branching and is early.

'KLENI10117' differs from the male parent 'TW1' (unpatented), by having medium-sized flowers and very good branching, while 'TW1' has large flowers and good branching.

'KLENI10117' differs from the commercial variety 'Darla Pink' (unpatented) by having very good branching, medium long leaves, and good suitability for a smaller (such as 10.5 cm) pot, while 'Darla Pink' has good branching, long leaves and is most suitable for a growth in a larger (such as 12.0 cm) pot.

We claim:

1. A new and distinct variety of New Guinea *Impatiens* plant named 'KLENI10117' as shown and described herein.

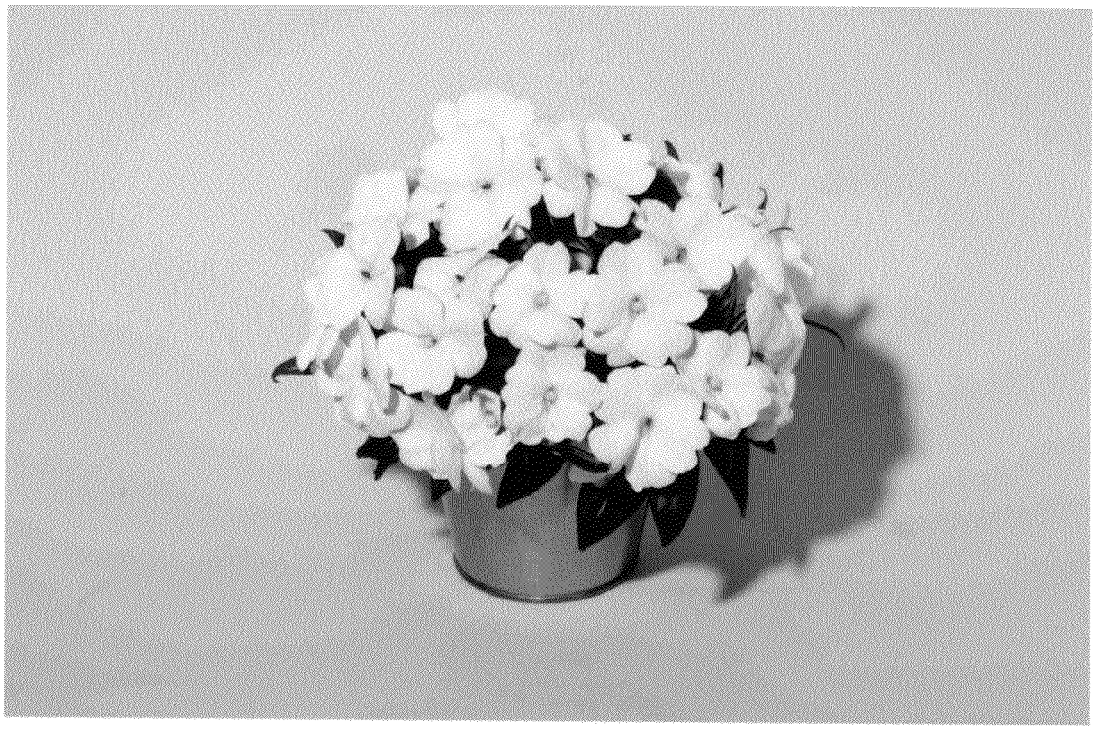

* * * * *